(12) United States Patent
Papadakis

(10) Patent No.: US 8,691,499 B2
(45) Date of Patent: Apr. 8, 2014

(54) METHOD OF DETECTING MOLECULES

(75) Inventor: Stergios Papadakis, Ellicott City, MD (US)

(73) Assignee: The Johns Hopkins University, Baltimore, MD (US)

(*) Notice: Subject to any disclaimer, the term of this patent is extended or adjusted under 35 U.S.C. 154(b) by 389 days.

(21) Appl. No.: 13/015,020

(22) Filed: Jan. 27, 2011

(65) Prior Publication Data

US 2011/0115505 A1    May 19, 2011

Related U.S. Application Data

(62) Division of application No. 12/168,258, filed on Jul. 7, 2008, now Pat. No. 7,906,316.

(60) Provisional application No. 60/948,015, filed on Jul. 5, 2007.

(51) Int. Cl.
  *C12Q 1/68* (2006.01)
  *C12M 1/36* (2006.01)
  *G01N 27/00* (2006.01)
  *B82Y 15/00* (2011.01)

(52) U.S. Cl.
  CPC ............. *G01N 27/00* (2013.01); *C12Q 1/6816* (2013.01); *B82Y 15/00* (2013.01)
  USPC .......... 435/4; 435/6.1; 435/283.1; 435/287.2; 422/82.01

(58) Field of Classification Search
  None
  See application file for complete search history.

(56) References Cited

U.S. PATENT DOCUMENTS

| | | | |
|---|---|---|---|
| 4,661,235 A | 4/1987 | Krull et al. | |
| 5,911,871 A | 6/1999 | Preiss et al. | |
| 6,267,872 B1 | 7/2001 | Akeson et al. | |
| 6,458,327 B1 | 10/2002 | Vossmeyer | |
| 6,746,594 B2 | 6/2004 | Akeson et al. | |
| 6,807,842 B2 | 10/2004 | Williams et al. | |
| 6,933,121 B2 | 8/2005 | Schuster et al. | |
| 6,960,298 B2 | 11/2005 | Krotz et al. | |
| 7,101,671 B2 | 9/2006 | Gao | |
| 7,192,752 B2 | 3/2007 | Xu et al. | |
| 7,226,738 B2 | 6/2007 | Hanna | |
| 2002/0094526 A1* | 7/2002 | Bayley et al. | ..... 435/6 |
| 2005/0009004 A1 | 1/2005 | Xu et al. | |
| 2006/0019247 A1 | 1/2006 | Su et al. | |
| 2007/0128423 A1 | 6/2007 | Belfort et al. | |

OTHER PUBLICATIONS

Lohndorf et al., Microfabricated high-performance microwave impedance biosensors for detection . . . , 2005 American Inst. of Phys. Appl.Phys.Lett. 87, 243902 (2005).
Ling, Addressable Nanopore Array Devices: Nanofabricatlon and DNA Translocation, Brown, Public date prior to Jul. 7, 2007.
Seethaler, Nanopore Method Could Revolutionize Genome Sequencing, UCSD Official web page of the University of California, San Diego, Apr. 6, 2006.
The Nanopore Project, Center for Biomolecular Science & Engineering, Jack Baskin School of Engineering, UC Santa Cruz, Jan. 2005, CBSE.

* cited by examiner

*Primary Examiner* — Betty Forman
(74) *Attorney, Agent, or Firm* — Noah J. Hayward

(57) ABSTRACT

Method of detecting molecules, using a sensor having a membrane layer having parallel pores extending through the membrane layer and incorporating therein probe molecules that bind with corresponding target molecules when present in the pores, electrodes, and an ionic solution in contact with the electrodes and the pores, wherein the electrodes are energized to induce an electrical current in the solution through the pores, wherein the electrical current induces an electrical parameter in the electrodes that is indicative of a through-pore electrical impedance of the pores, wherein the through-pore electrical impedance is increased when there is probe-to-target molecule binding in the pores relative to when there is an absence of such binding.

7 Claims, 15 Drawing Sheets

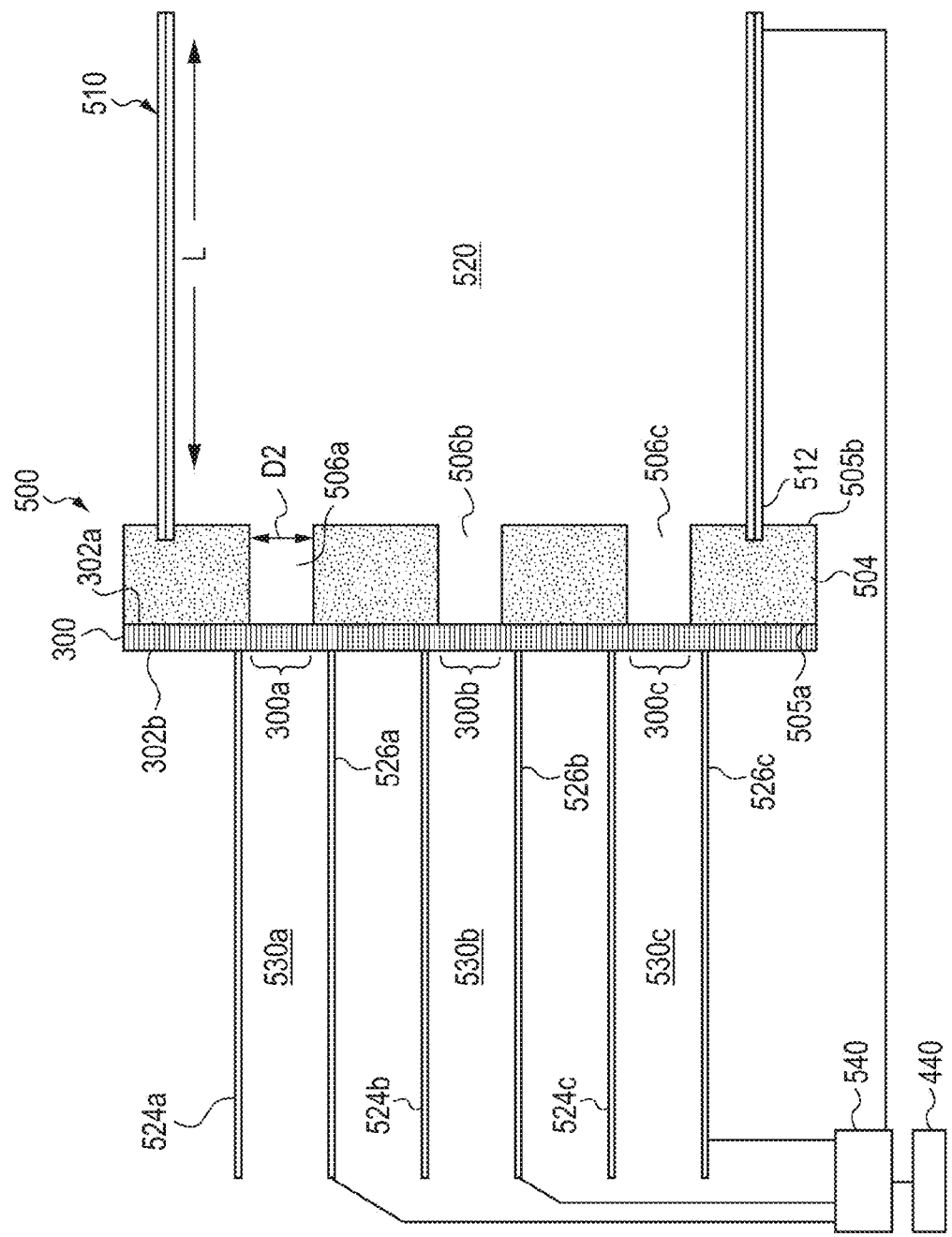

PORE DIAMETER 20-50 nm
(BROKEN AT ANGLE)

PORE DIAMETER 50-80 nm
(CLEAVED EDGE)

METHOD OF DETECTING MOLECULES

This application is a divisional of U.S. application serial no. 12/168,258, filed Jul. 7, 2008, which issued as U.S. Pat. No. 7,906,316 on Mar. 15, 2011, and which claims benefit of U.S. Provisional Application No. 60/948,015, filed Jul. 5, 2007, the entire contents of each being hereby incorporated by reference in its entirety.

CROSS-REFERENCE TO RELATED APPLICATIONS

This application is a divisional of U.S. application Ser. No. 12/168,258, filed Jul. 7, 2008, which claims benefit of U.S. Provisional Application No. 60/948,015, filed Jul. 5, 2007, the entire contents of each being hereby incorporated by reference in its entirety.

BACKGROUND OF THE INVENTION

1. Field of the Invention

The present invention relates to molecular sensors and methods related thereto.

2. Background

The development of various methods for nucleic acid detection and the detection of nucleic acid amplification products has led to advances in the detection, identification, and quantification of nucleic acid sequences in recent years. Nucleic acid detection is potentially useful for both qualitative analyses, such as the detection of the presence of defined nucleic acid sequences, and quantitative analyses, such as the quantification of defined nucleic acid sequences. For example, nucleic acid detection may be used to detect and identify pathogens; environmental monitoring; detect genetic and epigenetic alterations that are linked to defined phenotypes; diagnose genetic diseases or the genetic susceptibility to a particular disease; assess gene expression during development, disease, and/or in response to defined stimuli, including drugs; as well as generally foster advancements in the art by providing research scientists with additional means to study the molecular and biochemical mechanisms that underpin cellular activity. See U.S. Pat. No. 7,226,738.

In 1953, Watson and Crick suggested the concept of double stranded DNA. They had some significant discoveries. (1) deoxyribonucleic acid (DNA) molecules were composed of two anti-parallel poly-nucleic acid chains. (2) There were rules for paring the four bases—Chargaff et al. analyzed the base compositions of DNA molecules by chromatograph from many organisms, and found that the numbers of A and T were equal, while the numbers of C and G were also equal. So they suggest there exist four possible base pairs: A-T, T-A, G-C and C-G. (3) The connection of the two chains were through hydrogen bounds—the surface of the base pairs goes through and was roughly perpendicular to the axis. Two and three hydrogen bounds can form between the A-T and G-C pairs, respectively. Meanwhile, hydrophobic force also contributes to stabilize the DNA double helixes. (4) Because all the base pairs follow these rules, every chain can have random sequences. However, once the sequence of one of the chains is determined, the other one must have the corresponding nucleotide sequences. See U.S. Pat. No. 7,101,671.

As the DNA double helix is maintained by hydrogen bonds and hydrophobic force, factors, such as heat, pH, organic solvent, etc., which can destroy hydrogen and hydrophobic bonds, thus denaturing DNA double helixes to random single chain threads. The annealing between denatured DNA single chains through pairing is called hybridization. Hybridization can occur between homologous DNA molecules as well as homologous DNA and ribonucleic acid (RNA) molecules. During hybridization, the two complementary single-stranded DNA chains form double-stranded hybrids through non-covalent bounds. When the sequence of one of the chains is known, the existence of its complementary chain in an unknown DNA sample can be detected through hybridization. See U.S. Pat. No. 7,101,671.

Nucleic acid detection technology generally permits the detection of defined nucleic acid sequences through probe hybridization, that is, the base-pairing of one nucleic acid strand with a second strand of a complementary, or nearly complementary, nucleic acid sequence to form a stable, double-stranded hybrid. Such hybrids may be formed of a RNA segment and a DNA segment, two RNA segments, or two DNA segments, provided that the two segments have complementary or nearly complementary nucleotide sequences. (As is well known, a molecule of DNA or RNA possesses directionality, which is conferred through the 5' 3' linkage of the sugar-phosphate backbone of the molecule. Two DNA or RNA molecules maybe linked together through the formation of a phosphodiester bond between the terminal 5' phosphate group of one molecule and the terminal 3' hydroxyl group of the second molecule. See U.S. Pat. No. 6,933,121.

A known method for gene analysis to analyze DNA sequences in non-homogenous system is through DNA hybridization. Under sufficiently stringent conditions, nucleic acid hybridization may be highly specific, requiring exact complementarily between the hybridized strands. Typically, nucleic acid hybrids comprise a hybridized region of about eight or more base pairs to ensure the binding stability of the base-paired nucleic acid strands. Hybridization technology permits the use of one nucleic acid segment, which is appropriately modified to enable detection, to "probe" for and detect a second, complementary nucleic acid segment with both sensitivity and specificity. In the basic nucleic acid hybridization assay, a single-stranded target nucleic acid (either DNA or RNA) is hybridized, directly or indirectly, to a labeled nucleic acid probe, and the duplexes containing the label are quantified. Both radioactive and non-radioactive labels have been used. See U.S. Pat. No. 7,226,738.

Several methods have been advanced as suitable means for detecting the presence of low levels of a target nucleic acid in a test sample. One category of such methods is generally referred to as target amplification, which generates multiple copies of the target sequence, and these copies are then subject to further analysis, such as by gel electrophoresis, for example. Other methods generate multiple products from a hybridized probe, or probes, by, for example, cleaving the hybridized probe to form multiple products or ligating adjacent probes to form a unique, hybridization-dependent product. Still other methods amplify signals generated by the hybridization event, such as a method based upon the hybridization of branched DNA probes that have a target sequence binding domain and a labeled reporting sequence binding domain. See U.S. Pat. No. 7,226,738.

Techniques have been developed recently to meet the demands for rapid and accurate detection of pathogens, such as bacteria, viruses, parasites, and fungi, for example, as well as the detection of normal and abnormal genes. While all of these techniques offer powerful tools for the detection and identification of minute amounts of a target nucleic acid in a sample, they all suffer from various problems. For example, recognized disadvantage associated with current nucleic acid probe technologies is the lack of sensitivity of such assays when the target sequence is present in low copy number or dilute concentration in a test sample. In many cases, the presence of only a minute quantity of a target nucleic acid must be accurately detected from among myriad other nucleic acids that may be present in the sample. The sensitivity of a detection assay depends upon several factors: the ability of a probe to bind to a target molecule; the magnitude of the signal that is generated by each hybridized probe; and the time period available for detection. Another recognized disadvantage associated with current nucleic acid probe technologies is the reliance on fluorescence or radioactivity for nucleic acid detection.

Specifically, gene-probe assays may use a label that is either toxic or requires substantial expertise and labor to use. Radiolabeling is one of the most commonly used techniques because of the high sensitivity of radiolabels. But the use of radiolabeled probes is expensive and requires complex, time consuming, sample preparation and analysis and special disposal. Alternatives to radioactivity for labeling probes include chemiluminescence, fluorimetric and colorimetric labels, but each alternative has distinct disadvantages. Colorimetry is relatively insensitive and has limited utility where minute amounts of sample can be obtained. Samples must also be optically transparent. Fluorimetry requires relatively sophisticated equipment and procedures not readily adapted to routine use. Chemiluminescence, although versatile and sensitive when used for Southern blots, northern blots, colony/plaques lift, DNA foot-printing and nucleic acid sequencing, is expensive, and is not well-adapted for routine analysis in the clinical laboratory.

Other disadvantages of conventional sensors, such as gel micro-arrays, include difficulties with optical read-out, which include difficulties with aligning fluorescence spots with pads, and distinguishing a large a background signal from a signal of interest. Moreover, fluorescent tagging requires additional sensitive steps (after isolating target molecules from a sample, it must be tagged with a fluorescent molecule. In addition the instruments are bulky and expensive.

Accordingly, there is a need for rapid, sensitive, and standardized nucleic acid detection apparatuses and methods that can detect low levels of a target nucleic acid in a test sample that do not rely on fluorescence or radioactivity. These needs, as well as others, are met by the inventions of this application.

SUMMARY OF THE INVENTION

The present invention satisfies the above needs and provides other advantages, including, for example, use of electrical measurement in a simpler and more robust manner compared to optical techniques of conventional systems. This eliminates the disadvantages of conventional optical read-out and fluorescent tagging.

The invention provides an apparatus and related methods for detecting/sensing molecules of interest, i.e., target molecules. Exemplary target molecules include nucleic acid molecules comprising single strand DNA and RNA molecules.

An aspect of the invention includes a method for detecting oligonucleotides from a target DNA or RNA polynucleotide.

In a further aspect, the invention provides a method for detecting the presence or absence of mutations in a target DNA sequence.

In another aspect, the invention provides a method for detecting mutations in a target DNA polynucleotide.

In another aspect, the invention provides a method for detecting DNA or RNA in a test sample.

In another aspect, the invention provides a method for detecting the presence of pathogens in a test sample.

In still a further aspect, the invention provides a method for detecting mRNA expression in a test sample.

In still a further aspect, the invention provides a method for detecting an oligonucleotide synthesized from a target DNA sequence.

In still a further aspect, the invention provides a method for detecting multiple reiterated oligonucleotides from a target DNA or RNA polynucleotide.

In still a further aspect, the invention provides a method for detecting methylated cytosine residues at a CG site near a target gene.

In still a further aspect, the invention provides a method for detecting a target molecule indicative of a malignant cell, such as a cell infected with a pathogen, a precancerous cell, a cancer cell or a cell comprising a mutation of a heredity gene.

In still a further aspect, the invention provides a method for detecting a pathogen, or a target molecule indicative of a pathogen.

The present invention also provides kits for the molecule, e.g., oligonucleotide, detection methods described herein. In one aspect, for example, the invention provides reagent containers, which contain various combinations of the components described herein. These kits, in suitable packaging and generally (but not necessarily) containing suitable instructions, contain one or more components used in the oligonucleotide detection methods. The kit may also contain one or more of the following items: nucleotides and a control DNA or a control RNA polynucleotide. The kit may also contain reagents mixed in appropriate amounts for performing the methods of the invention. The reagent containers preferably contain reagents in unit quantities that obviate measuring steps when performing the subject methods.

Probe and Target Molecules

The terms "probe molecule(s)" and "target molecule(s)" are referred to through-out the present description.

Exemplary probe molecules used in embodiments of the present invention comprise, but are not limited to, nucleic acid molecules, including DNA, single strand DNA (ssDNA), RNA, and single strand RNA (ssRNA). The target molecules that bind to such exemplary nucleic acid probe molecules comprise nucleic acid molecules of a type complementary to the probe molecules, e.g., complementary ssDNA or ssRNA, where such binding includes hybridization. With respect to binding between single strand nucleic acid molecules, the term "complement" or "complementary" refers to the strand of nucleic acid molecule that will hybridize to a first nucleic acid molecule to form a double stranded molecule. Thererfore corresponding types of nucleic acid probe and target molecules are complementary types.

Exemplary target molecules used in the present invention are taken from and/or derived from sample material containing, e.g., nucleic acid molecules. Examples of sample materials include bacterial cells, bacterial cell homogenates, fungal cells, protist cells, viral plaques obtained from plates, viral material (e.g., DNA or RNA) isolated by cesium chloride centrifugation, human buccal swabs, saliva, urine, human blood, animal blood, purified human blood cells, purified animal blood cells, blood cell homogenates, human tissue, animal tissue and plant materials such as plant tissue, leaves, roots, stems, and fruits. Thus, the term "sample" encompasses any material which contains or from which can be derived target molecules. The target molecules may purified nucleic acid molecules or, alternatively, crude preparations which contain nucleic acid molecules.

Detection of Microbes, Pathogens

In the present invention, by using specific sequences of DNA or RNA that are characteristic of target microbes, pathogens can be unambiguously identified/detected, regardless of their cultivable states, by direct analysis of contaminated food or water samples. As used herein, "microbes" is intended to include, but is not limited, to unicellular organisms, eukaryotic cells, bacteria, viruses, cyanobacteria, fungi, yeast, molds, prions and archebacteria. Definitive data may be obtained regarding food and water quality, and the time-consuming culturing step associated with coliform counts is reduced or eliminated. In addition, distinctions can be made between different coliform bacteria, e.g. pathogenic v. non-pathogenic bacteria. Examples of pathogens that can be detected using the invention include, but are not limited to, bacteria such as *Salmonella* sp., *Escherichia coli*, *Klebsiella pneumoniae*, *Bacillus* sp., *Shigella* sp., *Campylobacter* sp., *Helicobacter pylori*, *Vibrio* sp., Chlamydia, Giardia, parasites such as Naegleria and Acanthamoeba and viruses such as Hepatitis and poliomyelitis.

Detection of Genetic Variations

The invention may be employed to detect genetic variations or genetic mutations or genetic mutants associated with different disorders or diseases. The terms "mutation," "mutant" and "variation" may be used interchangeably and, as used herein, is intended to reference deletions, additions, insertions, inversions and replacement of nucleic acid sequences or bases in the sequence.

Examples of hereditary diseases that can be diagnosed by the detection of genetic variations or hereditary genes include cystic fibrosis, muscular dystrophy, sickle cell anemia and other hematopoietic disorders, phenylketonuria, thalassemia, hemophilia, a.sub.1-antitrypsin deficiency, disorders of lipoprotein metabolism and inherited forms of cancer.

Malignant cell transformation is a multistep process resulting from the progressive acquisition of structural alterations at multiple genetic loci which are involved in the regulation of cell growth and can also be diagnosed by the detection of genetic variations. It has been well documented that gain-of-function mutations, found in dominantly-acting proto-oncogenes, are often accompanied by loss-of-function mutations in tumor suppressor genes in human malignant cells. Several tumor suppressor genes have been identified whose mutation or deletion appears to be critical for the development of human cancers, among them, p53, RB and WT1, whose gene products are found in nucleus and which function as regulators of gene transcription (reviewed in Kaelin et al., Cellular proteins that can interact specifically with the retinoblastoma susceptibility gene product. In Origin of human cancer: A comprehensive review, Brugge, J., Curran, T., Harlow, E., McCormik, F. eds. (Cold Spring Harbor Laboratory Press), pp.423-431 (1991); Lewin, Cell 64:303-312 (1991); Marshall, Cell 64:313-326 (1991); Weinberg, Science 254:1138-1146 (1991); Haber and Housman, Adv. Cancer Res. 59:41-68 (1992); Vogelstein and Kinzler, Cell 70:523-526 (1992); Levine, Annu. Rev. Biochem. 62:623-651 (1993)). Therefore, the qualitative or quantitative analysis of human genes is also desirable for analysis of amplified oncogenes, detection of genetic defects and in the determination of gene expression levels in tumors.

An embodiment of the present invention is an apparatus for sensing molecules. The apparatus operates, essentially, based on all-electronic processing, and comprises: a membrane layer having parallel pores extending through the membrane layer and incorporating therein probe molecules that bind with corresponding target molecules when present in the pores; electrodes; and an ionic solution in contact with the electrodes and the pores, wherein the electrodes are energized to induce an electrical current in the solution through the pores, wherein the electrical current induces an electrical parameter in the electrodes that is indicative of a through-pore electrical impedance of the pores, wherein the through-pore electrical impedance is increased when there is probe-to-target molecule binding in the pores relative to when there is an absence of such binding.

A method embodiment comprises exposing pores in a baseline membrane layer to a target solution containing target molecules so as to cause binding between the probe molecules and the target molecules if they are of the corresponding type; passing an electrical current, in an ionic solution, through the pores to generate an electrical parameter indicative of a test through-pore electrical impedance of the pores, where the test through-pore electrical impedance is a function of whether there is probe-to-target molecule binding in the pores; measuring the electrical parameter; and determining whether there is probe-to-target molecule binding in the pores based on the measured electrical parameter.

Further related method, system and apparatus embodiments are apparent from the description below.

BRIEF DESCRIPTION OF THE DRAWINGS

Various embodiments are described below with reference to the drawings.

FIG. 5 is a cross-sectional view of another example sensor of the present invention, which involves a method of multiplexing between multiple pixels of a sensor array.

FIGS. 8B-8C show a porous structure resulting from anodization, while FIG. 8D shows a membrane suspended over a pixel opening formed through an underlying substrate.

DETAILED DESCRIPTION OF THE DRAWINGS

1. Porous Membrane Layer Embodiments

Figure 1A:
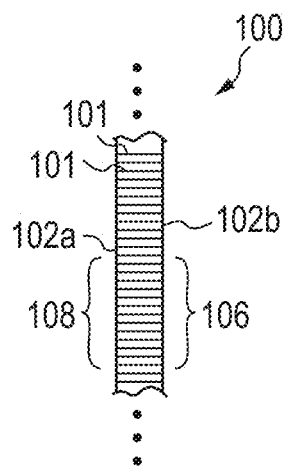
FIG. 1A is a cross-sectional view an example membrane layer of the present invention that can be used in a molecular sensor of the present invention.
Figure 1B:
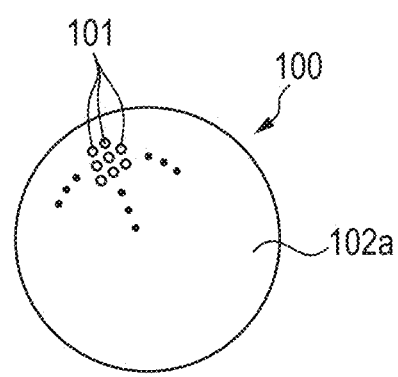
FIG. 1B is a top view of the membrane layer of FIG. 1A.

FIG. 1A is a cross-sectional view and FIG. 1B is a top view of an example membrane layer 100, also referred to as a porous layer or disk 100, of the present invention. Membrane layer 100 (and alternative arrangements and embodiments thereof) represents a component of an apparatus for sensing/detecting target molecules, as described below. With reference to FIGS. 1A and 1B, membrane layer 100 includes opposing faces 102a, 102b and has formed therein multiple parallel pores 101 extending through the membrane layer, i.e., between faces 102a and 102b. Pores 101 extend through membrane layer 100, in a direction that is perpendicular to the planes of faces 102a, 102b, so that volumes 106 and 108 on either side of the membrane layer are in fluid communication with each other through the pores. Pores 101 are spread across faces 102a, 102b as depicted in FIG. 1B. In an embodiment, membrane layer 100 and the pores therein are formed of alumina. In another arrangement, the membrane layer comprises silicon, or polycarbonate. Membrane layer 100 has attached thereto probe molecules such that the probe molecules occupy or are fixedly incorporated into the pores 104, as depicted in FIGS. 2A and 2B.

Figure 2A:
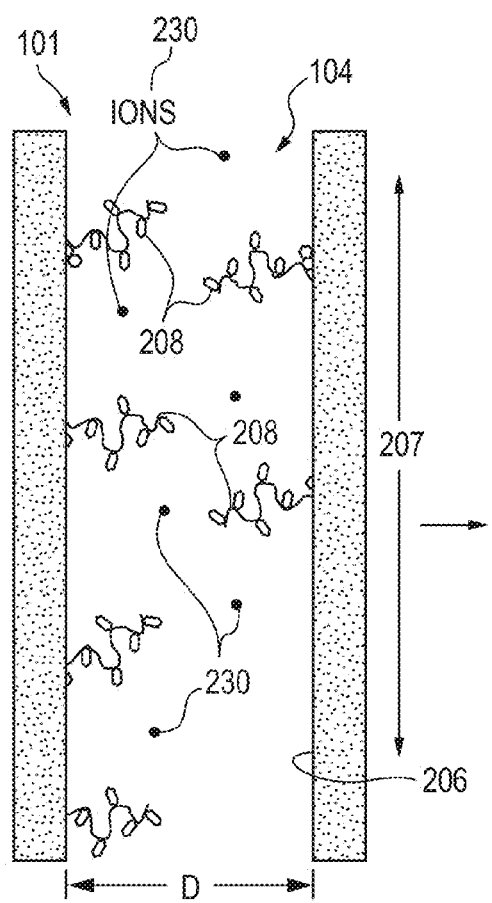
FIGS. 2A and 2B are exploded cross-sectional views of one of the pores through the membrane layer of FIGS. 1A and 1B.
Figure 2B:
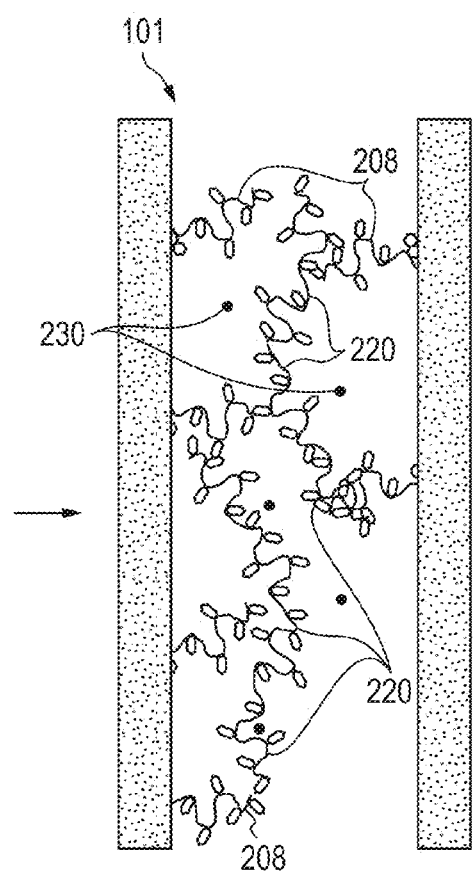

FIGS. 2A and 2B are exploded cross-sectional views of one of pores 101 formed through membrane layer 100. With reference to FIG. 2A, each of pores 101 includes a peripheral pore wall 206, formed from a portion of membrane layer 100, which defines a pore opening or void 104 that is substantially cylindrical in shape and that extends through the membrane layer. Pore wall 206 defines a diameter D of pore opening 104, having an exemplary size in a range of between 10 nanometers and 200 nanometers. Numerous probe molecules 208 are attached, e.g., bonded, to pore wall 206 along a length 207 thereof so as to extend, and thereby be incorporated, into opening 104 of the pore. In an embodiment, probe molecules 208 are covalently bonded to pore wall 206.

With reference to FIG. 2B, probe molecules 208 are selected to be of a specific type that tends to bind, i.e., has a strong affinity for binding, e.g., chemically, with a corresponding specific type of target molecule 220, when, and if, the target molecule of the corresponding type are present in the pores 101 and sufficiently close to the probe molecules as to cause such binding, as depicted in FIG. 2B. This binding is referred to as probe-to-target molecule binding within pore 101. Examples of such binding between probe and target molecules include, but are not limited to, covalent, non-covalent, or by hybridization (e.g. between nucleic acid molecules) type bonding, or any other type of molecular bonding. Exemplary probe and target molecules bonded to the pore walls are described above As will be described more fully below in connection with FIG. 4A, an aspect of the present invention is determining a presence, or conversely, an absence, of target molecules 220 in pores 101 based a movement or flow of ions 230, or ionic current, through the pores, which varies as a function of whether there is probe-to-target molecule binding in the pores, and, more specifically, the concentration of target molecules incorporated into the pores.

Figure 3A:
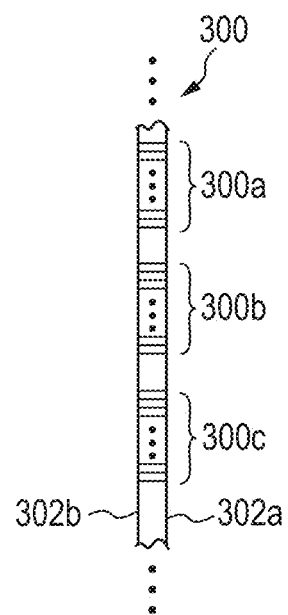
FIG. 3A is a cross-sectional view and FIG. 3B is a top view of another example membrane layer having different areas of parallel pores each incorporating different types of probe molecules, according to the present invention.
Figure 3B:
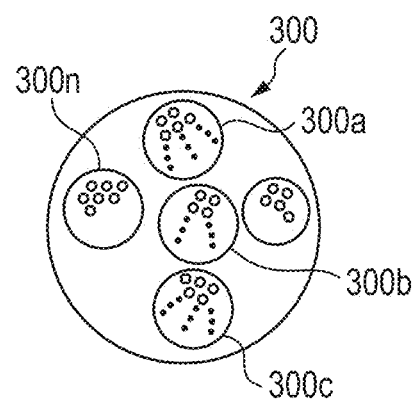

FIG. 3A is a cross-sectional view and FIG. 3B is a top view of another example membrane layer 300, also referred to as a porous layer or disk 300, of the present invention. Membrane layer 300 (including opposing faces 302a, 302b) is constructed similarly to membrane layer 100, except that membrane layer 300 has an array of different areas of parallel pores 300a-300n formed through the membrane layer and spread across an area of membrane layer 300. The pores of the different areas 300a-300n have incorporated therein probe molecules as described above in connection with FIGS. 1 and 2. However, different areas of pores 300a-300n incorporate different types of probe molecules, respectively, so that the different areas of pores bind to different types of target molecules. In other words, the pores of a given one of the areas (e.g., 300a) incorporates therein probe molecules of a type (e.g., typeA) common across the pores of that given area but that is different from the types (e.g., typeB, typeC . . . typeN) of probe molecules corresponding to the other areas (e.g., 300b, 300c . . . 300n), such that the different areas of pores bind with their correspondingly different types of target molecules. In this way a single membrane layer can be use to detect multiple types of target molecules.

2. Sensor Apparatus Embodiments
2.1 First Embodiment

Figure 4A:
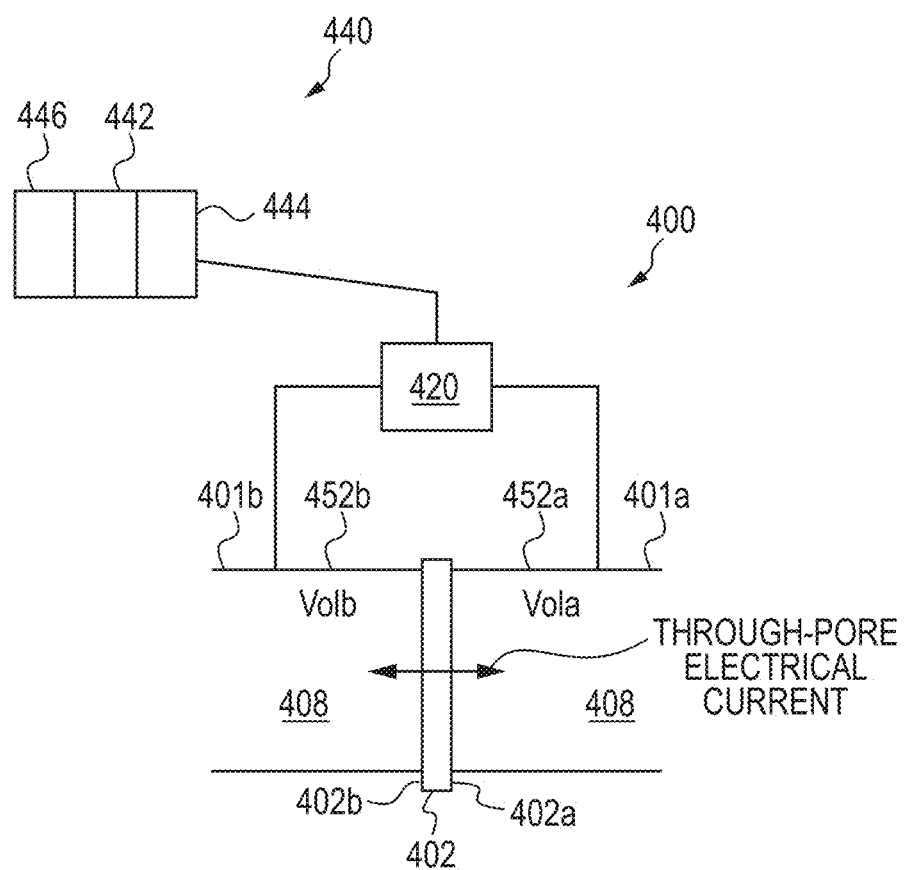
FIG. 4A is an example apparatus or sensor for sensing/detecting target molecules, according to the present invention.

FIG. 4A is an example apparatus 400 (also referred to as a sensor 400) for sensing/detecting target molecules, according to the present invention. Sensor 400 includes spaced apart electrodes 401a, 401b, a membrane layer 402 between the spaced electrodes, an ionic solution 408 in contact with both of the electrodes and the membrane layer, a source meter 420 electrically coupled to the electrodes, and a computer system 440 electrically coupled with the source meter.

Membrane layer 402, similar to membrane layer 100, includes parallel pores extending through the membrane layer between opposing faces 402a, 402b of the layer. Probe molecules are attached to the pores of membrane layer 402 so as to be fixedly incorporated therein, as described above. In the arrangement of FIG. 4A, the pores of membrane layer incorporate a single type of probe molecule corresponding to a single type of target molecule. However, in another arrangement, membrane layer 402 incorporates different areas of pores having different types of probe molecules incorporated therein, respectively.

Spaced electrodes 401a, 401b, tubular in shape, have respective ends, 452a, 452b fixed against respective opposing faces 402a, 402b of membrane layer 402. In this arrangement, membrane layer face 402a and electrode 401a together define a volume VolA adjacent face 402a, while membrane layer face 402b and electrode 401b together define a volume VolB adjacent face 402b. Volumes VolA and VolB are in fluid communication with each other only through the parallel pores of membrane layer 402. The electrodes may be provided in other configurations, and need not be fixed against the membrane layer. However, it is important that an electrical current carried by ionic 408 solution between the spaced electrodes 401 on either side of the membrane layer pass only through the pores of the membrane layer and not around the membrane layer as by, e.g., leakage. Otherwise, impedance measurements of the membrane layer will not be a strong function of pore geometry, as discussed below. Accordingly, the sensor housing (not shown) and electrodes are constructed to avoid such stray leakage.

Ionic solution 408 occupies volumes VolA and VolB and the pores of membrane layer 402. The composition of the electrodes, e.g., gold, platinum, etc., should be selected to be compatible with the probe and target molecules, the sizes of the pores, and the ionic solution. The concentration of the ionic solution needs to be sufficiently high to generate measurable signals (e.g., currents and voltages), as described below. An exemplary ionic solution is aqueous sodium chloride.

Source meter 420, electrically coupled to electrodes 401a, 401b, includes circuits that energize the electrodes by applying across them either a voltage (i.e., an applied voltage), or, alternatively, a current (i.e., an applied current), so as to cause an electrical current in solution 408 to flow between the electrodes through the pores of membrane layer 402. Exemplary source meters are the 2400 series source meters manufactured by Keithley. This electrical current through membrane layer 402 results from a movement of ions in ionic solution 408, including movement of ions in/through the pores of membrane layer 402, responsive to the applied voltage, or alternatively, applied current. In the case of an applied voltage, the resulting electrical current through the pores generates or induces a corresponding voltage across electrodes 401a, 401b. In the case of an applied current, the resulting electrical current through the pores generates or induces a corresponding current across electrodes 401a, 401b. The magnitude of the generated voltage or current is a function of the through-pore impedance of the pores of membrane layer. Accordingly, by applying a known current/voltage to electrodes 401a, 402b, and measuring the resulting generated voltage/current, the through-pore impedance can be determined.

Source meter 420 also includes circuits that measure either the current, or alternatively, the voltage generated in electrodes 401a, 401b responsive to the electrical current through membrane layer 402 that results from either the applied voltage, or alternatively, applied current, respectively. Specifically, if source meter 420 applies a current across electrodes 401a, 401b, then the source meter measures a corresponding voltage across the electrodes. Alternatively, if source meter 420 applies a voltage across electrodes 401a, 401b, then the source meter measures a corresponding current across the electrodes. In either case, the measured voltage or current is a function of and, thus, indicative of the through-pore impedance of the pores of the membrane layer. The through-pore impedance is a function, and thus indicative, of whether there is, or is not, binding between the probe molecules and the target molecules and, thus, the presence, or absence of target molecules in the pores, respectively. In an arrangement, source meter 420 applies an a.c. voltage/current and measures a corresponding a.c. current/voltage, from which electrical impedance of the membrane layer (i.e., the impedance of the pores of the membrane layer) can be determined. An exemplary range of a.c. frequency is between 1 Hz and 1 MHz. In another arrangement, a d.c. voltage/current can be applied and the corresponding current/voltage measured.

Source meter 420 can be replaced with any similar circuits as described above for applying a voltage/current and measuring the resulting generated current/voltage, as would be appreciated by one having relevant skill in the art after having read the present description.

Meter 420 communicates with a computer 440, including a processor 442, memory 444, and a display 446 coupled with each other. Computer 440 can be hand-held processor and display, suitable, for example, for incorporation into a field kit for sensing molecules, a personal computer, or any other processor based system. Computer 440 executes computer programs and/or includes circuitry to support methods of the present invention in a manner that would be understood by one having appropriate skill in the art after having read the present application. Computer 440 records, processes, and displays electrical parameter measurements provided by meter 420. For example, computer 440 records the above-mentioned current and/or voltage measurements from meter 420. Computer 440 also compares different measurements made by meter 420 over time, and displays results of these comparisons.

2.1.1 Discussion of Through-Pore Impedance

With reference to FIGS. 2A, 2B and FIG. 4, the above-mentioned electrical impedance presented by the membrane layer, or more specifically, the pores of the membrane layer, is a function of several factors, including geometry, ionic concentration, and a frequency of the voltage or current applied by electrodes 401a, 401b. The geometry factors include pore diameter D, the numbers of parallel pores, the types and sizes of probe molecules and target molecules attached to the pores and each other, and a distance between electrodes 401a, 401b.

In a baseline configuration of membrane layer 402 having an absence of binding between probe and target molecules in each of the pores, i.e., where only probe molecules occupy the pores as depicted in FIG. 2A, ions (e.g., depicted at 230) of ionic solution 408 move relatively freely in the pores because only the probe molecules occupy the pores. Therefore, the pores present a relatively low through-pore physical resistance to the movement of ions, which results in a corresponding relatively low through-pore electrical impedance, e.g., resistance, referred to as a baseline through-pore electrical impedance.

Conversely, in a configuration of membrane layer having a presence of probe-to-target molecule binding in the pores, as depicted in FIG. 2B, there is more material, i.e., both probe and target molecules, filling the pores. In the same way that less fluid can flow through a partially clogged pipe, fewer ions can flow freely through the partially clogged pore relative to the case where there is an absence of probe-to-target molecule binding in the pores. This decrease in physical conductance results in a corresponding decrease in electrical conductance, or inversely, a corresponding increase in electrical impedance of the pores relative to the baseline configuration (FIG. 2A).

The multiple parallel pores of the membrane layer 402 exhibit an aggregate or combined through-pore electrical impedance. This aggregate through-pore impedance is a combination of the individual through-pore impedance of each of the many thousands of pores contacting ionic solution 408. The voltage/current measured by meter 420 is a function, and thus representative, of the aggregate through-pore impedance. A typical range of aggregate electrical impedance is between 50 ohms and 5000 ohms, depending on the factors listed above.

Diameter D of pores 101 is sized in relation to a size of probe molecules 208 and a size of target molecules 220 so as to produce a measurable difference in through-pore electrical impedance between configurations of membrane layer 402 having (i) an absence of probe-to-target binding in the pores (FIG. 2A), which represents a baseline through-pore electrical impedance against which other through-pore impedances may be compared, and (ii) a presence of probe-to-target molecule binding in the pores (FIG. 2B). The present invention uses this measurable difference as an indication of, and thereby to detect, the presence, or alternatively, the absence, of target molecules in pores 104.

2.1.2 Example Operation

Membrane layer 402 is provided in its baseline configuration, i.e., in the absence of probe-to-target binding in the pores. Source meter 420 energizes electrodes 401a, 401b by applying a current/voltage across the electrodes so as to induce an electrical current between the electrodes through ionic solution 408 and the pores of the baseline membrane layer. Meter 420 measures a corresponding electrical parameter, e.g., voltage/current, induced by the electrical current, where the electrical parameter is a function of the baseline (aggregate) through-pore impedance of the membrane layer and, thus, indicative of the absence of any probe-to-target binding. Computer 440 records, processes (if necessary), and displays the measurement as a display signal in any suitable form. The signal may be representative of a quantity derived from the electrical parameter, such as an impedance value.

Next, membrane layer 402 is exposed to target molecules so as to induce probe-to-target molecule binding, if any, in the pores. After such exposure, the pores will either (i) incorporate target molecules, bound to the probe molecules, because the target molecules to which the pores were exposed were of a corresponding type that would cause binding between the probe molecules and the target molecules, or (ii) not incorporate target molecule because the probe and target molecules were not of a corresponding type (i.e., there is an absence of probe-to-target molecule binding in the pores). The membrane layer 402 is said to be in its test configuration.

Source meter 420 again energizes electrodes 401a, 401b, by applying a current/voltage across the electrodes, so as to induce an electrical current in ionic solution 408 between the electrodes through pores of the test membrane layer. Meter 420 measures a corresponding electrical parameter, e.g., voltage/current, induced by the electrical current, indicative of a test through-pore electrical impedance of the membrane layer and, thus, whether there is probe-to-target molecule binding in the pores. Computer 440 records and displays the measurement. Computer 440 can display a magnitude of the measured paremter over time alone or overlayed against a baseline parameter, calculate an impedance value based on the measured parameter and display the value numerically, or in graphical form, and so on.

As mentioned above, probe-to-target molecule binding in the pores increases the through-pore impedance relative to an absence of such binding. Therefore, an indicated test through-pore impedance (i.e., a through-pore impedance as indicated by the measured electrical paremeter) that is greater than an indicated baseline through-pore impedance indicates the presence of the target molecule. Conversely, an indicated test through-pore impedance that is substantially the same as an indicated baseline through-pore impedance indicates an absence of target molecules. In other words, a change, in this case increase, in the through-pore impedance is indicative of the presence of target molecules. Processor 440 can determine the absence or presence of target molecules based on the measurements, e.g., by comparing, and display a result indicative of the presence or absence of the target molecules.

Figure 4B:
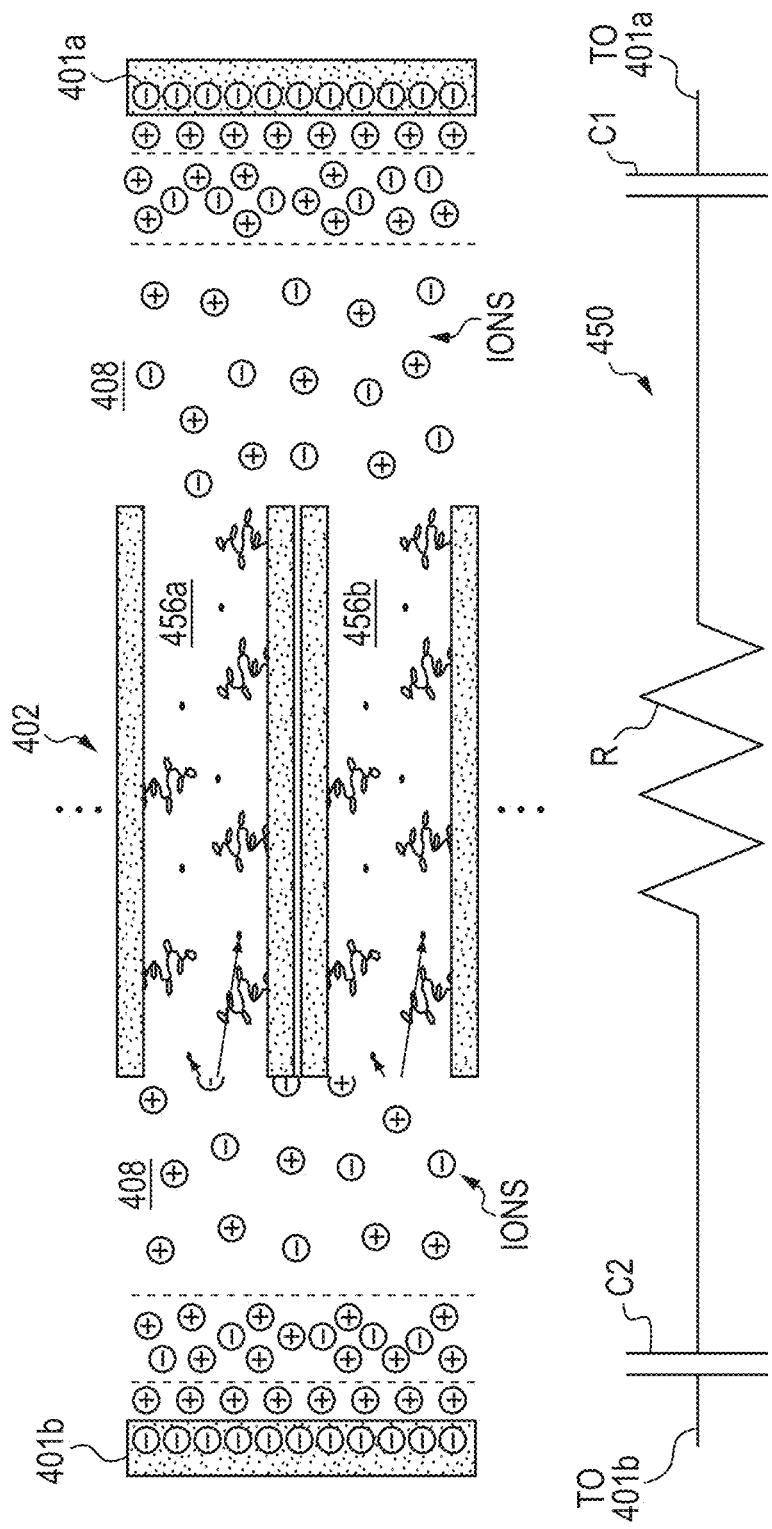
FIG. 4B is an illustration of a partial molecular schematic and an equivalent circuit of the apparatus of FIG. 4A.

FIG. 4B is an illustration of an equivalent circuit 450 of sensor apparatus of FIG. 4A (the equivalent circuit is depicted below a portion of a molecular schematic of apparatus 400). Equivalen circuit 450 includes an equivalent resistor R the magnitude of which is dominated by the the aggregate through-pore impedance of multiple individual pores 456a, 456b of membrane layer 402. Capacitors C1, C2 represent electrode-solution interfaces.

Figure 4C:
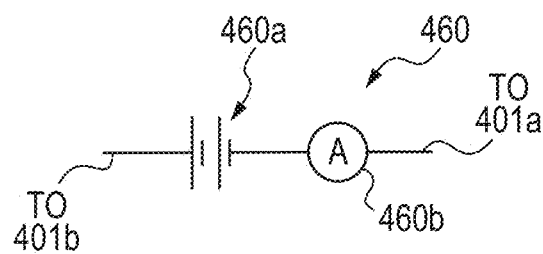
FIGS. 4C and 4D are example circuits of a source meter of the apparatus of FIG. 4A.

FIG. 4C is an example circuit 460 of source meter 420. Circuit 460 includes a voltage source 460a for applying a voltage across electrodes 401a, 401b, connected in series with an ammeter 460b for measuring a corresponding electrical current that generated in the electrodes by the electrical current in solution induced by the applied voltage, as mentioned above.

Figure 4D:
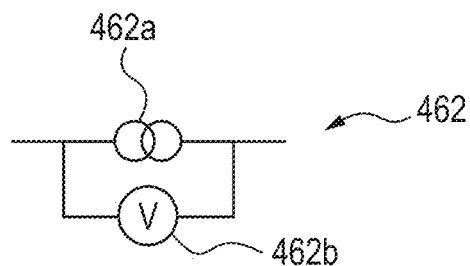

FIG. 4D is an example circuit 462 of source meter 420. Circuit 462 includes a current source 462a for applying a current across electrodes 401a, 401b, connected in parallel with an voltmeter 462b for measuring a corresponding voltage across the electrodes, as mentioned above.

2.2 Second Embodiment

FIG. 5 is a cross-sectional view of an example sensor 500 of the present invention. Sensor 500 includes membrane layer 300 having different areas of pores 300a-300n, each incorporating a type of probe molecule different from the other areas of pores. A substrate layer 504, having opposing faces 505a, 505b, underlies membrane layer 300 so that face 505a is adjacent membrane layer face 302a. Substrate layer 300 includes through-holes 506a-506n formed therein so as to be aligned, and in fluid communication, with corresponding ones of the areas of pores 300a-300n. A diameter D2 of each of holes 506i is sufficiently large to encompass a large number, e.g., many thousands, of the pores of the corresponding area of pores 300i. For example, each of holes 506i can have a diameter between, e.g., 10 microns and 200 microns, and thereby encompass between, e.g., 200,000 and 2,000,000, pores.

Sensor 500 includes a single tubular electrode 510 of length L having an end 512 adjacent substrate face 505b. In this example end 512 is fixed against substrate face 505b so that the end 512 encircles an area of the substrate face encompassing holes 506a-506n (and areas of pores 300a-300n). Accordingly, electrode 510 and substrate face 505b together define a volume 520 in fluid communication with holes 506 and the pores of membrane layer 300. Electrodes 510 and 524 may comprise gold, platinum, or any other suitable conductive electrode material.

Sensor 500 also includes an array of multiple tubular electrodes 524a-524n each adjacent (i) face 302b of membrane layer 300 (i.e., so that they are positioned on the other side of membrane layer 300 from electrode 510), and (ii) a corresponding one of the areas of pores 300a-300n. In this example arrangement, an end 526a-526n of each electrode is fixed against face 302b so as to be aligned with and enclose at least a portion of a corresponding one of areas of pores 300a-300n, as depicted in FIG. 5. In this manner, electrodes 524a-524n, along with corresponding areas 300a-300n, define channels or volumes 530a-530n, which are in fluid communication with only the pores of each of the corresponding areas of pores 300a-300n. In this manner, each of channels 530i is in fluid communication with volume 520 through a corresponding one of area of pores 300i. An ionic solution occupies the volumes 520, channels 530 and the pores in each of the ares 300. Together, each of through-holes 506i, the corresponding area of pore 300i, and the corresponding one of electrodes 524i (and its corresponding channel 530i) form what is referred to as a measurement "pixel."

A source meter 540, similar to source meter 420, electrically coupled to electrodes 510 and 524, includes circuits that energize electrode 510 and electrodes 524 so as to produce an electrical current in solution through the pores of membrane layer 300. Source meter 540 includes circuits, including multiplexers, that are configured to selectively energize electrode 510 concurrent with all of electrodes 524, or only selected ones of electrodes 524, i.e., to energize different combinations of electrodes. For example, source 540 may energize electrode 510 and (i) each of electrodes 524a-524n concurrently so as to produce electrical currents through all of the corresponding areas of pores 300a-300n, or (ii) only electrode 524a so as to produce electrical currents only through area of pores 300a, or only electrode 524b so as to produce an electrical current only across the area of pores 300b, or only electrodes 524a and 524b, etc. In this manner, electrode 510 together with a selected one, or more, of electrodes 524a-524n are energized so as to produce an electrical current through the area pores (e.g., one, ore more, of areas 300a-300n) corresponding to (i.e., adjacent to) the selected one, or more, of electrodes 524a-524n.

Source meter 540, includes circuits for measuring electrical parameters, e.g., voltage when a corresponding current is applied across the electrodes by the source meter or current when a corresponding voltage is applied across the electrodes by the source meter, indicative of the through-pore impedances of each of the areas of pores 300a-300n, in the manner described above in connection with FIG. 4A. Processor and display system 440, coupled with source meter 540, record, process and display results of the measurements.

In an exemplary operation, source meter selectively energizes electrodes corresponding to each of the areas of pores 300a-300n in sequence, i.e., one after the other, and, at each sequential energization, measures an electrical parameter indicative of the through-pore impedance for the area of pores presently conducting/passing electrical current responsive to the energized electrodes. Initial baselining and then subsequent testing of each of the different areas of pores 300a-300n may be performed as described above in connection with FIG. 4A.

Method Flowcharts

Figure 6A:
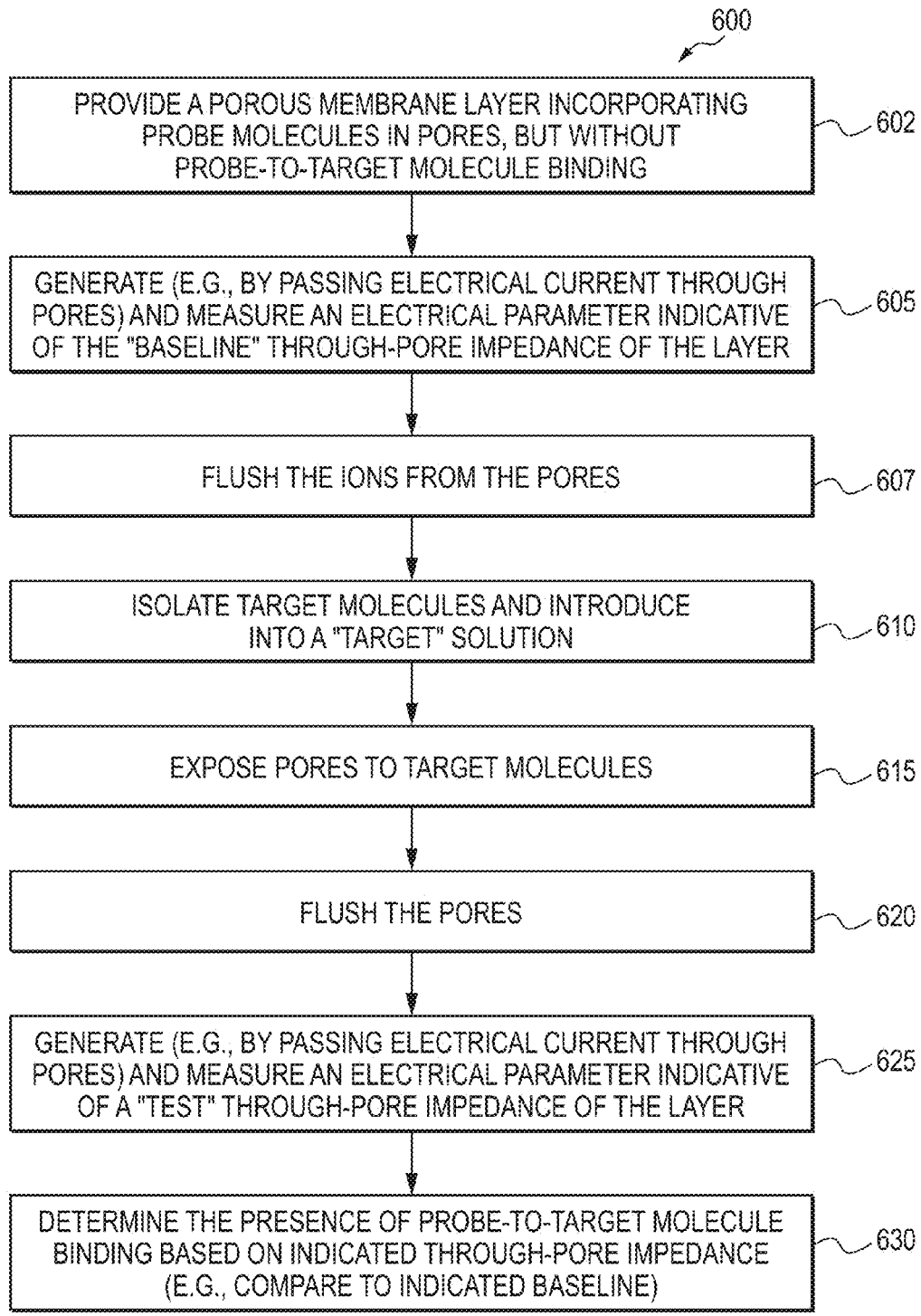
FIGS. 6A, 6B and 6C are flowcharts of example methods of the present invention.

FIG. 6A is a flow chart of an example method 600 of sensing target molecules that can be achieved using the aforementioned exemplary sensors and related techniques.

A first step 602 includes providing a membrane layer (e.g., membrane layer 100) having parallel pores (e.g., pores 101) extending through the membrane layer, which has probe molecules (e.g., ssDNA) incorporated into the pores. The probe molecules are of a type that binds with target molecules of a corresponding type (e.g., complementary ssDNA) when the target molecules are present in the pores. There is no such probe-to-target molecule binding in the membrane layer provided in this step 602. Therefore, the pores of the membrane layer provided in this step 602 exhibit a through-pore impedance in the absence of probe-to-target molecule binding that is referred to as a baseline through-pore impedance, which may be represented, indirectly or directly, by a measured baseline electrical parameter (e.g., current or voltage).

A next step 605 includes measuring an electrical parameter (e.g., current or voltage) indicative of the baseline through-pore impedance. This includes passing an electrical current through the pores in the medium of an ionic solution to generate an electrical parameter that is a function of, and thus, indicative of, the baseline through-pore electrical impedance, and measuring that electrical parameter. Exemplary substeps for this step 605 are essentially the same as those described in step 625 below, and are not repeated twice for purposes of brevity.

A next step 607 include flushing the ionic solution from the pores using, e.g., a buffer solution.

A next step 610 includes isolating target molecules (e.g., ssDNA from a sample, such as those listed above) and introducing same into a buffer solution, referred to as a "target" solution, which may be a liquid or a gas.

A next step 615 includes exposing the pores of the membrane layer provided in step 602 to the target solution containing the target molecules, so as to cause binding between the probe molecules and the target molecules if they are of the corresponding type. This step may include flowing the target solution through the pores of the membrane, and may result in no probe-to-target molecule binding if the probe molecules and target molecules in solution are not of the corresponding type.

A next step 620 includes flushing the target solution from, or out of, the pores of the membrane layer using, e.g., a buffer solution. Further flushing with water may also be performed.

A next step 625 includes measuring an electrical parameter indicative of a through-pore impedance of the exposed pores resulting from step 615 (or 620). The through-pore impedance indicated in this step is referred to as a "test" through-pore impedance because it represents a test for the presence of target-to-probe molecule binding that may have occurred in step 615. This step 625 includes applying a voltage/current to electrodes on opposing sides of the membrane layer so as to cause an electrical current to flow, by way of an ionic solution (i.e., through movement of ions), between the electrodes and through the pores, which in turns generates the electrical parameter (e.g., current if a voltage was applied and voltage if a current was applied) in the electrodes. The electrical parameter is a function and, thus, indicative of the through-pore electrical impedance of the exposed pores. The through-pore impedance is a function and, thus, indicative, of whether there is, or is not, binding between the probe molecules and the target molecules and, thus, the presence, or absence of target molecules in the pores, respectively. The through-pore impedance indicated in this step 625 is an aggregate of concurrent multiple individual through-pore impedances.

A next step 630 includes determining whether there are target molecules present in the pores, i.e., whether this is probe-to-target molecule binding in the pores, based on the test through-pore impedance indicated in step 625. This step includes comparing the test through-pore electrical impedance indicated in step 625 to the baseline through-pore electrical conductance indicated in step 602. If the through-pore impedance indicated in step 625 is higher than its corresponding baseline value from step 602, then this it is determined that there is probe-to-target binding, i.e., target molecules are present. If the through-pore impedance indicated in step 625 is substantially the same as its corresponding baseline value from step 602, then this it is determined that there is no probe-to-target binding, i.e., target molecules are not present. Thus, an increase in the through-pore impedance from step 602 to step 625 indicates the presence of target molecules of a type corresponding to the probe molecules.

Figure 6B:
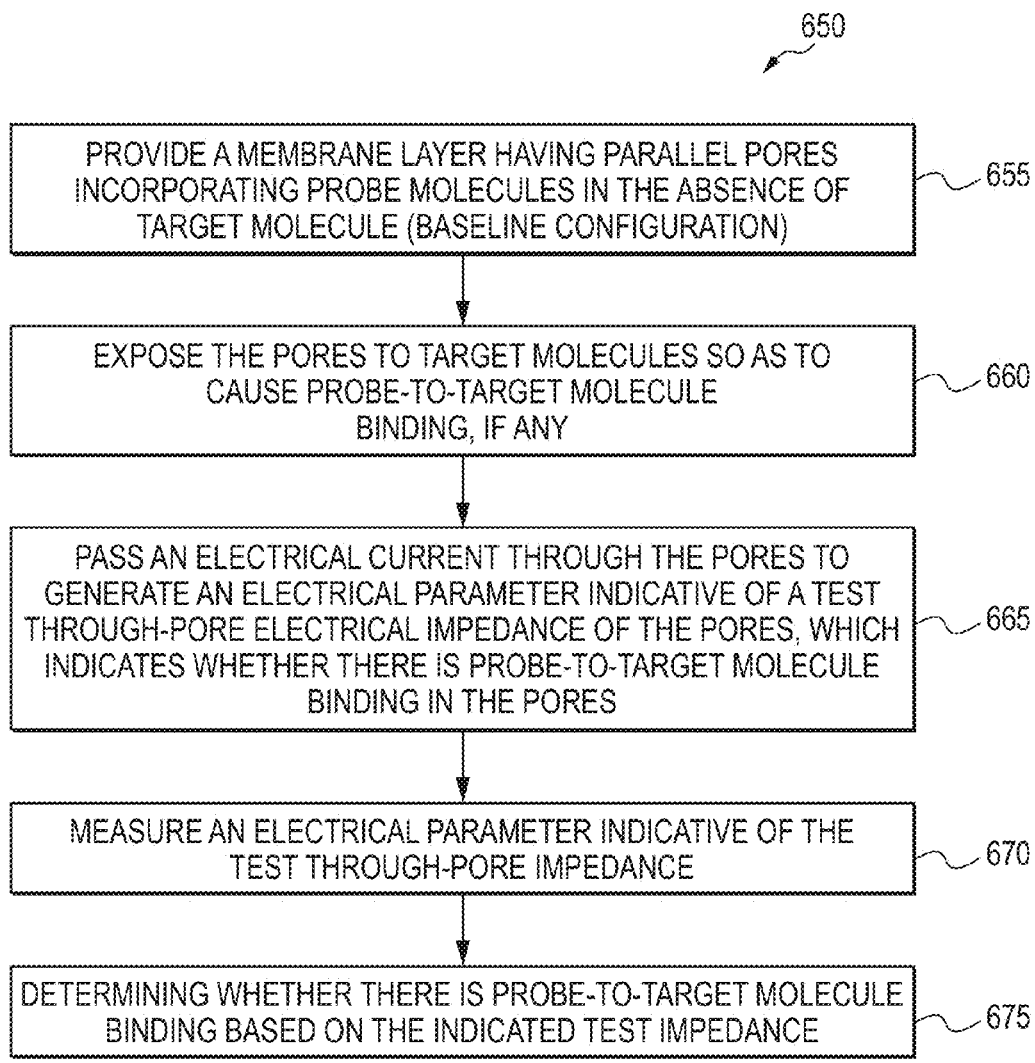

FIG. 6B is a flow chart of another example method 650 of sensing target molecules that can be achieved using the aforementioned exemplary sensors and related techniques.

A first step 655 includes providing a membrane layer having parallel pores incorporating probe molecules in the absence of target molecules, i.e., in a baseline configuration.

A next step 660 includes exposing the pores in the baseline configuration to target molecules so as to cause binding between the probe molecules, if any.

A next step 665 includes passing an electrical current through the pores in an ionic solution to generate an electrical parameter indicative of the a test through-pore impedance of the pores, which is indicative of whether there is binding between the probe molecules and the target molecules.

A next step 670 includes measuring the electrical parameter indicative of the test through-pore impedance.

A next step 675 includes determining whether there is probe-to-target molecule binding in the pores based on the measured electrical parameter indicative of the test through-pore impedance.

Figure 6C:
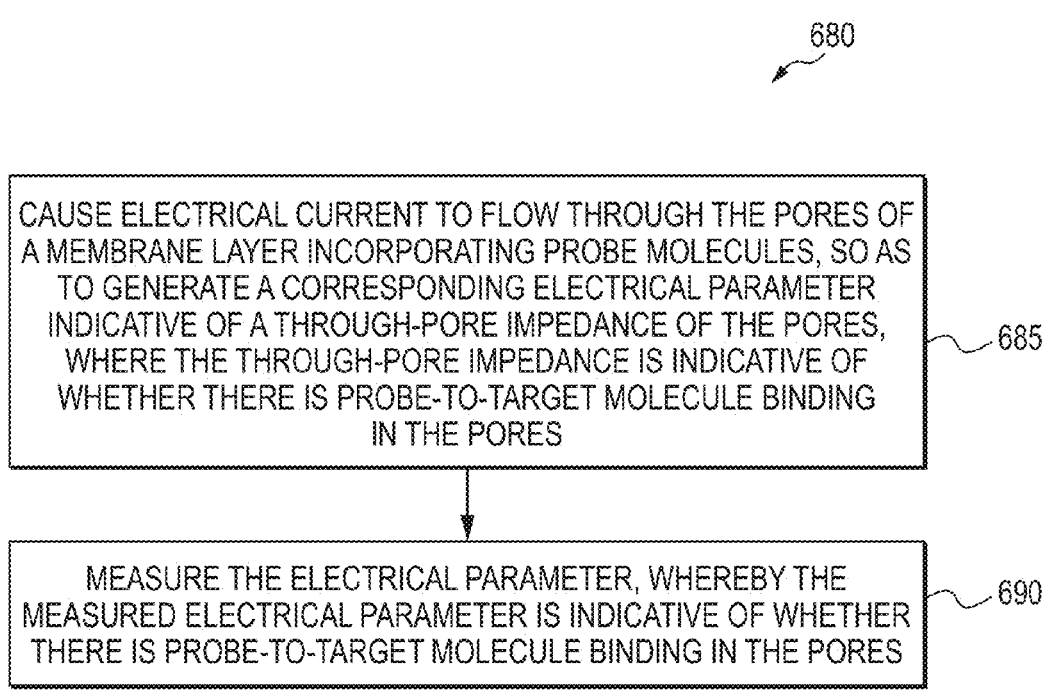

FIG. 6C is a flow chart of another example 680 of sensing target molecules using a membrane layer having parallel pores extending through the membrane layer and incorporating therein probe molecules that bind with corresponding target molecules when present in the pores.

A first step 685 includes causing a an electrical current in an ionic solution to flow through the pores of the membrane layer so as to generate a corresponding electrical parameter that is a function of a through-pore impedance of the pores, where the through-pore impedance is a function of whethere there is probe-to-target molecule binding the pores.

A next step 690 includes measuring the electrical parameter, whereby the measured electrical parameter is indicative of whether there is probe-to-target molecule binding in the pores.

The steps of either of the flowcharts depicted in FIGS. 6A, 6B and 6C may be permuted, some may be omitted, and some may be combined with others to form different methods within the scope of the present invention.

Membrane Layer Fabrication

An example method of fabricating a membrane layer and its supporting substrate layer of the present invention (e.g., as depicted in FIG. 5), is now described with reference to FIGS. 7A-7E.

Figure 7A:
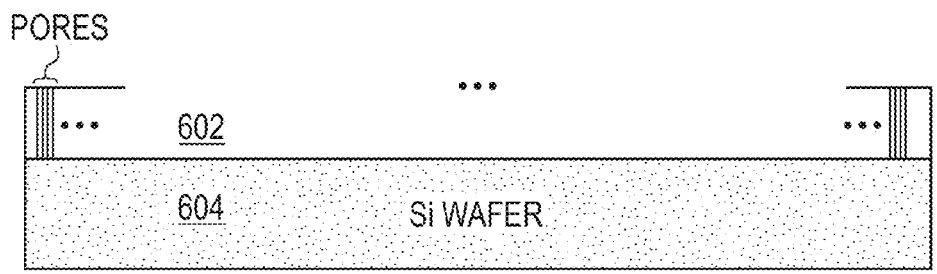
FIGS. 7A-7E are illustrations of successive example fabrications stages of a membrane layer and substrate of the present invention.

In FIG. 7A, a layer of aluminum (Al) 602 approximately 3 microns thick is physical vapor deposited onto a substrate layer 604 made of, e.g., silicon (Si). Then aluminum layer 602 is anodized to create pores, thereby converting the pure aluminum to aluminum oxide ($Al_2O_3$). The pores have diameters that are relatively constant along their lengths.

Figure 7B:

In FIG. 7B, a photoresist layer 606 is spun onto the substrate layer 604.

Figure 7C:
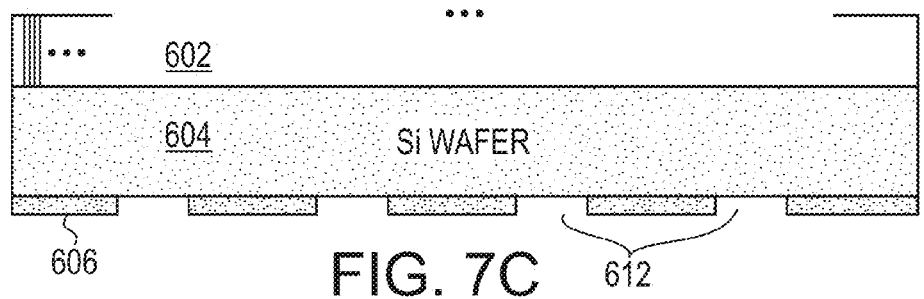

In FIG. 7C, photoresist layer 606 is exposed with an overlaid mask and then developed to produce openings 612 exposing underlying portions of Si layer 604.

Figure 7D:
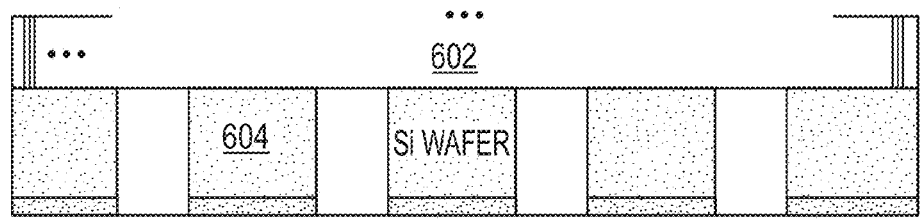

In FIG. 7D, the exposed portions of silicon layer 604 are removed using deep reactive ion etching (DRIE).

Figure 7E:
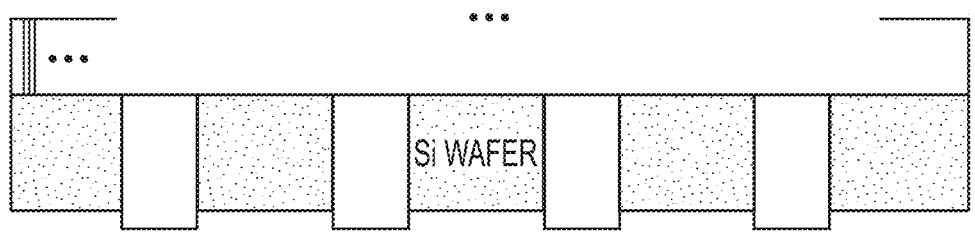

In FIG. 7E, residual photoresist is removed.

A method of covalently binding probe molecules to the membrane layer is now described. This method covalently binds probe molecules to the pore walls, so as to provide a membrane layer as required in, e.g., step 602 of method 600.

This method assumes a membrane layer made of alumina.

First, the membrane layer and its pores are cleaned using, e.g., oxygen plasma.

Next, the alumina layer and its pores are exposed to, e.g., (3-glycidoxypropyl) trimethoxysilane ("silane" "GPS") in toluene.

Next, the alumina layer is baked to drive covalent bonds between the silane molecules and the alumina, e.g., inner surfaces 206.

Next, amine-terminated probe molecules, in buffer solution, are flowed through the pores. In an example, the probe molecules are ssDNA terminated in an amine molecule. The amine portions of the probe molecules covalently bond to the silane molecules bonded to the tube walls.

Next, a buffer rinse is flowed through the pores, leaving the probe molecules bonded to the walls of the pores.

Figure 8A:
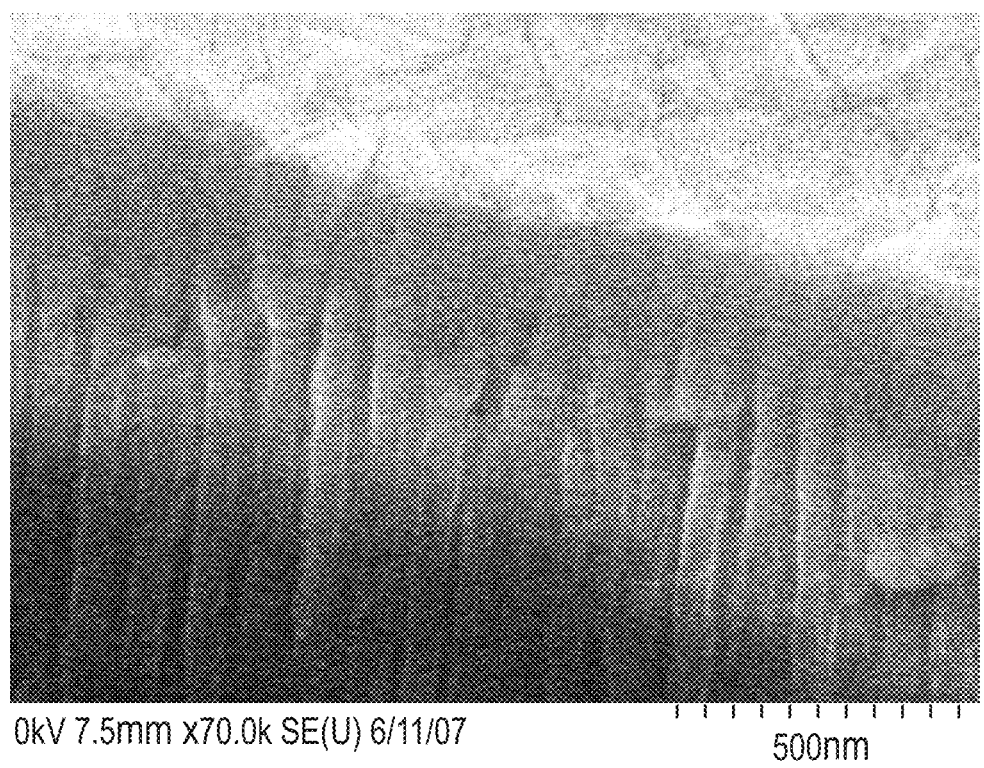
FIGS. 8A-8D are magnified images of a membrane layer fabricated using techniques of the present invention.
Figure 8B:
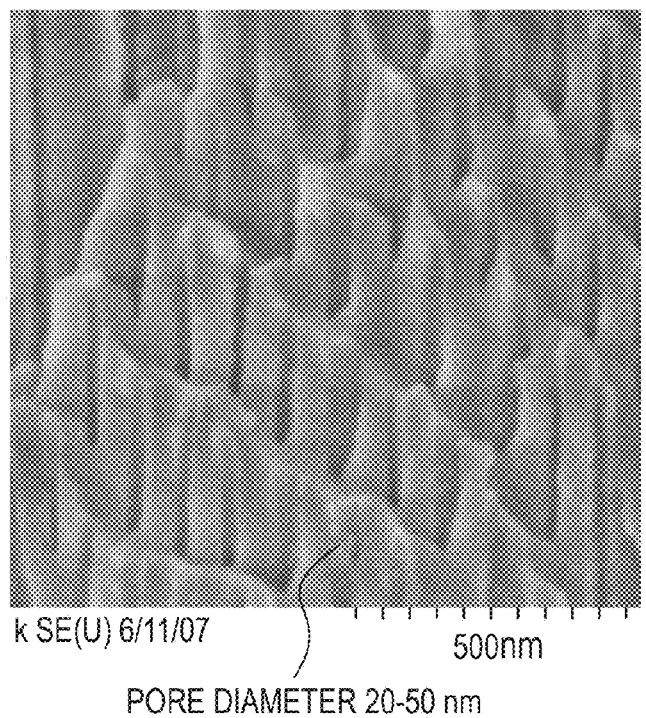
Figure 8C:
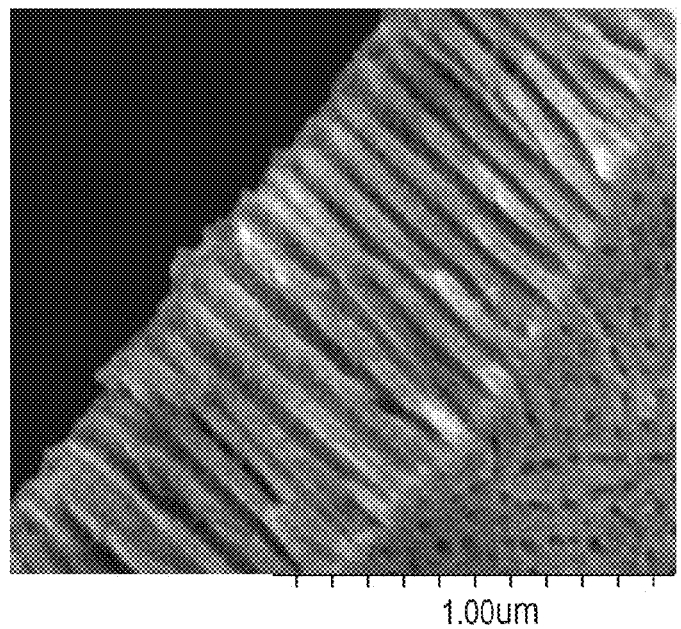

FIGS. 8A-8C are magnified images of an anodized aluminum membrane layer fabricated using techniques of the present invention.

FIG. 8A is an image of a cleaved edge of the membrane layer.

FIG. 8B is an image of pores broken at an angle and having diameters between 20-50 nanometers.

FIG. 8C is an image of pores having diameters in the 50-80 nanometer range.

Figure 8D:
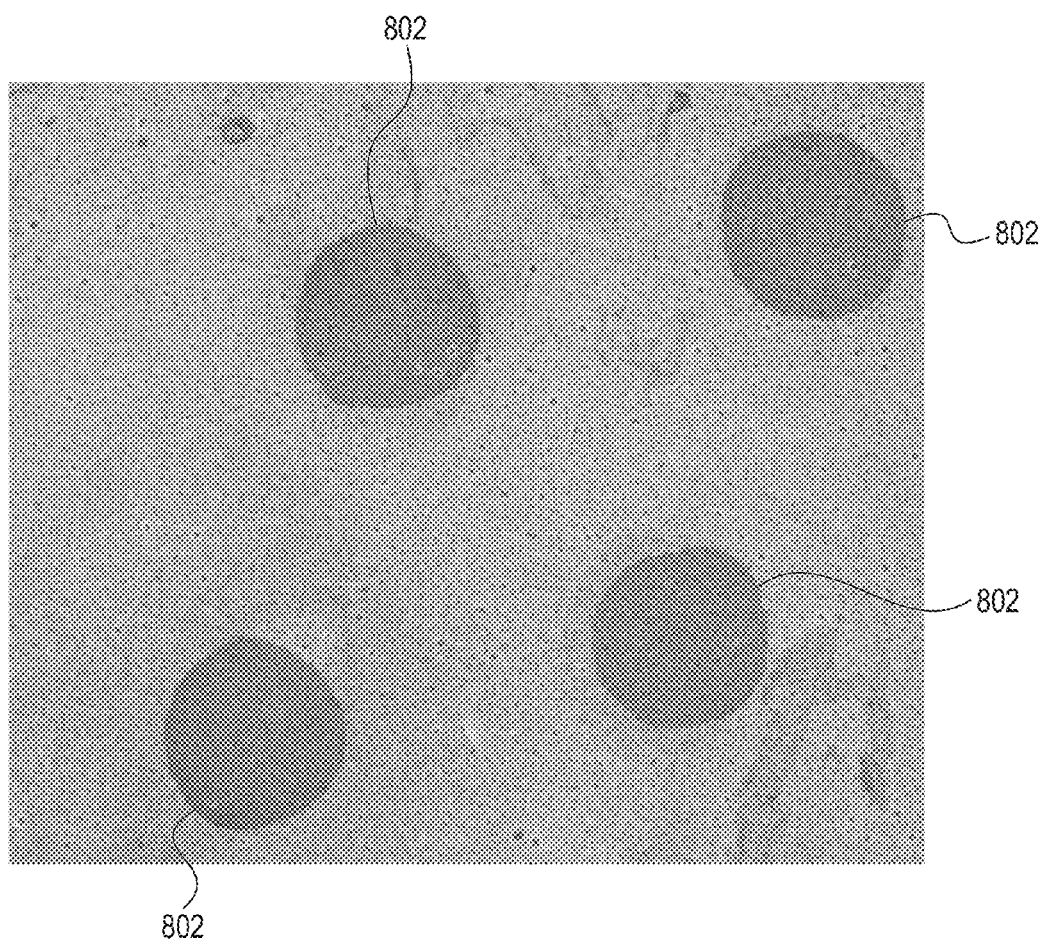

FIG. 8D is an image of a top face of a membrane layer having pores there-through. The opposing bottom face of the membrane layer is overlaying a substrate having through-holes formed therein. The dark regions 802 are shadows formed by the through-holes 802. Each dark region encompasses many thousands of pores.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A method of detecting target molecules using a membrane layer having opposing sides through which parallel pores extend, each of the pores having a sidewall to which probe molecules are fixed, the probe molecules being selected to bind with corresponding target molecules when the target molecules are present in the pores, the membrane layer being initially provided in a baseline configuration having an absence of probe-to-target molecule binding in the pores, the method comprising:

exposing the pores in the baseline configuration to a target solution containing target molecules so as to cause binding between the probe molecules and the target molecules if they are of the corresponding type;

flushing the pores using a buffer solution to remove the target solution from the pores;

subsequent to flushing of the pores, passing an electrical current, in an ionic solution, through the pores to generate an electrical parameter indicative of a test through-pore electrical impedance of the pores, where the test through-pore electrical impedance is a function of whether there is probe-to-target molecule binding in the pores;

measuring the electrical parameter; and determining whether there is probe-to-target molecule binding in the pores based on the measured electrical parameter.

2. The method of claim 1, wherein the test through-pore impedance represents an aggregate of multiple concurrent individual through-pore impedances of the pores.

3. The method of claim 1, wherein the baseline configuration of the membrane layer has a baseline through-pore impedance corresponding to the absence of probe-to-target molecule binding, said determining step comprising determining the presence of probe-to-target molecule binding in the pores if there is a difference between the measured electrical parameter and a baseline electrical parameter indicative of the baseline through-pore electrical impedance.

4. The method of claim 3, further comprising:

passing an electrical current, in an ionic solution, through the pores of the baseline configuration pores to generate the electrical parameter indicative the baseline through-pore electrical impedance; and measuring the electrical parameter indicative of the baseline through-pore electrical impedance.

5. The method of claim 1, wherein the probe molecules comprise single strand nucleic acid molecules which bind to target molecules that comprise single strand nucleic acid molecules that are complementary to the probe molecules.

6. A method of detecting target molecules using a membrane layer having parallel pores extending through the membrane layer, wherein probe molecules are attached to the membrane layer so as to be incorporated into the pores, the probe molecules being of a type selected to bind with target molecules of a corresponding type when present in the pores, the method comprising:

(a) providing the membrane layer in a condition where there is no binding in the pores between the probe molecules and the target molecules;

(b) passing an electrical current through the pores in an ionic solution to generate an electrical parameter indicative of a baseline through-pore electrical impedance;

(c) measuring the electrical parameter indicative of the baseline through-pore impedance;

(d) exposing the pores to a target solution containing target molecules so as to cause binding between the probe molecules and the target molecules if they are of a corresponding type;

(e) flushing the target solution out of the pores using a buffer solution to remove the target solution from the pores;

(f) passing an electrical current through the exposed pores in an ionic solution to generate an electrical parameter indicative of the through-pore electrical impedance of the exposed pores, which is indicative of whether there is binding between the probe molecules and the target molecules resulting from step (d), if any;

(g) measuring the electrical parameter from step (f);

(h) comparing the measured electrical parameters from steps (c) and (g); and (i) determining a presence of probe-to-target molecule binding in the pores based on said comparison step.

7. A method for sensing molecules using an apparatus comprising a membrane layer having a plurality of areas, each area comprising a plurality of pores extending through the membrane layer and each area incorporating therein different probe molecules within each of the pores, the probe molecules binding with corresponding target molecules when present in the pores, wherein the apparatus further comprises a common electrode adjacent one of the opposing sides of the membrane layer; and a plurality of area electrodes on the other of the opposing sides of the membrane layer, the method comprising:

exposing the membrane layer to an ionic solution comprising target molecules;

causing an electrical current in the ionic solution to flow through the pores of the membrane layer so as to generate a corresponding electrical parameter for each area that is a function of a through-pore impedance of the pores, where the through-pore impedance is a function of whether there is probe-to-target molecule binding the pores, wherein the electrical parameter represents an aggregate, concurrent through-pore electrical impedance for each area comprising the plurality of pores; and measuring the electrical parameter of selected ones of the different areas of pores, whereby the measured electrical parameter is indicative of whether there is probe-to-target molecule binding in the corresponding selected ones of the different areas of pores.

* * * * *